(12) United States Patent
Haas et al.

(10) Patent No.: US 6,297,408 B1
(45) Date of Patent: Oct. 2, 2001

(54) TWO-STAGE PROCESS FOR THE PRODUCTION OF 1,3-PROPANEDIOL BY CATALYTIC HYDROGENATION OF 3-HYDROXYPROPANAL

(75) Inventors: Thomas Haas, Frankfurt; Bernd Jaeger, Darmstadt; Joerg Sauer; Willi Hofen, both of Rodenbach; Rudolf Vanheertum, Kahl, all of (DE)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/786,501
(22) PCT Filed: Sep. 1, 1999
(86) PCT No.: PCT/US99/19980
§ 371 Date: Mar. 2, 2001
§ 102(e) Date: Mar. 2, 2001
(87) PCT Pub. No.: WO00/14041
PCT Pub. Date: Mar. 16, 2000

Related U.S. Application Data

(60) Provisional application No. 60/099,235, filed on Sep. 4, 1998.

(51) Int. Cl.$^7$ .............................. C07C 27/04; C07C 31/18
(52) U.S. Cl. ............................................. 568/862; 568/852
(58) Field of Search ..................................... 568/862, 852

(56) References Cited

U.S. PATENT DOCUMENTS

| 5,334,778 | * | 8/1994 | Haas et al. ........................... 568/862 |
| 5,364,984 | * | 11/1994 | Arntz et al. ......................... 568/862 |

* cited by examiner

*Primary Examiner*—Samuel Barts
*Assistant Examiner*—Elvis O. Price

(57) ABSTRACT

A two-stage process for producing 1,3-propanediol by first hydrogenating at a temperature of 30° C. to 80° C. in the presence of an oxide-supported metal hydrogenation catalyst. Second, the resulting reaction solution is hydrogenated at a temperature of 80° C. to 180° C. to a 3-hydroxypropanal conversion of substantially 100% in the presence of an activated carbon-supported metal hydrogenation catalyst.

10 Claims, No Drawings

TWO-STAGE PROCESS FOR THE PRODUCTION OF 1,3-PROPANEDIOL BY CATALYTIC HYDROGENATION OF 3-HYDROXYPROPANAL

This is a 371 of Application Ser. No. PCT/US99/19980 filed Sep. 1, 1999 which claims benefit of Provisional No. 60/099,235 filed Sep. 4, 1998.

BACKGROUND

This invention relates to an improved process for the production of 1,3-propanediol by catalytic hydrogenation of 3-hydroxypropanal.

1,3-Propanediol is used as a monomer unit for polyesters and polyurethanes and as a starting material for synthesizing cyclic compounds.

Various processes are known for the production of 1,3-propanediol via 3-hydroxypropanal (HPA) which start either from $C_2$ and $C_1$ structural units or from a $C_3$ structural unit, such as, for example, acrolein. When acrolein is used, it is first hydrated in aqueous phase in the presence of an acidic catalyst to form HPA. After removing the unreacted acrolein, the aqueous reaction mixture formed during hydration still contains, in addition to 85 wt % based on total organics of 3-hydroxypropanal, approximately 8 wt % 4-oxaheptane-1, 7-dial and further organic components in smaller proportions by weight. This reaction mixture is hydrogenated in the presence of hydrogenation catalysts to produce 1,3-propanediol. The 1,3-propanediol is recovered from the reaction mixture by distillation and/or extraction based methods known to those skilled in the art.

U.S. Pat. No. 5,334,778 discloses a two stage process for hydrogenating 3-hydroxypropanal which yields 1,3-propanediol having a residual carbonyl content, expressed as propionaldehyde, of below 500 ppm. The hydrogenation is carried out at 30° C. to 80° C. to a 3-hydroxypropanal conversion of 50 to 95% and then is continued at 100° C. to 180° C. to a 3-hydroxypropanal conversion of substantially 100%. Suitable hydrogenation catalysts therein include Raney nickel suspension catalysts, and supported catalysts based on platinum or ruthenium on activated carbon, $Al_2O_3$, $SiO_2$, or $TiO_2$ as well as nickel on oxide- or silicate-containing supports.

According to U.S. Pat. No. 5,015,789, very active nickel catalysts exhibit inadequate long-term stability, with a rapid drop in hydrogenation conversion and reaction speed upon repeated use of the catalyst. This results in frequent replacement of the entire catalyst packing, which is associated with known problems in the disposal and working up of compounds containing nickel. In addition, soluble nickel compounds can form and are released into the product stream, requiring further steps to separate the resulting contaminants.

Hydrogenation processes may be characterized by the conversions, selectivities, and space-time yields achievable therewith. Percent conversion of 3-hydroxypropanal is defined by:

$$X = \% \text{ Conversion of HPA} = \frac{\text{moles of HPA converted}}{\text{moles of HPA supplied}} \times 100$$

Selectivity of the hydrogenation process is a measure of the amount of converted 3-hydroxypropanal which is converted into the desired product:

$$\% \text{ Selectivity} = \frac{\text{moles of 1, 3-propanediol}}{\text{moles of HPA converted}} \times 100$$

The space-time yield is another important characteristic for continuous hydrogenation processes, stating the achievable quantity of product per unit time and reaction volume.

When hydrogenating 3-hydroxypropanal to 1,3-propanediol on a large industrial scale, it is vital, with regard to the economic viability of the hydrogenation process and the quality of the product, for conversion and selectivity to be as close as possible to 100%. The 1,3-propanediol may be separated from the water as well as remaining 3-hydroxypropanal and secondary products contained in the product stream by distillation after the hydrogenation. However, this distillative separation is rendered very difficult by residual 3-hydroxypropanal and secondary products and may even become impossible due to reactions between the residual 3-hydroxypropanal and 1,3-propanediol to yield acetals such as 2-(2'-hydroxyethyl)-1,3-dioxane (HED), which have a boiling point close to the boiling point of 1,3-propanediol. Thus, the lower the conversion and selectivity, the poorer the achievable product quality.

In order to produce 1,3-propanediol economically, it is also important for the catalyst to exhibit high activity for the hydrogenation of 3-hydroxypropanal. The objective should thus be to find a process in which the smallest possible quantity of catalyst is necessary for the production of 1,3-propanediol; i.e., it should be possible to achieve the greatest possible conversion of 3-hydroxypropanal to 1,3-propanediol with a small volume of catalyst.

Another important quality criterion for hydrogenation catalysts is their operational service life. Good catalysts should ensure high conversion and selectivity in the hydrogenation of 3-hydroxypropanal to 1,3-propanediol over the course of their service life.

SUMMARY OF THE INVENTION

The present invention provides an improved two-stage process for the production of 1,3-propanediol which comprises hydrogenating an aqueous solution of 3-hydroxypropanal using an oxide-supported metal hydrogenation catalyst in a first, low temperature, stage and continuing hydrogenation in a second, high temperature, stage using an activated carbon-supported (i.e., charcoal supported) metal hydrogenation catalyst. More specifically, the process of the present invention comprises hydrogenating an aqueous 3-hydroxypropanal solution at a temperature of between about 30° C. to 80° C., preferably about 40° C. to 80° C., to a conversion of greater than about 70% in the presence of a first hydrogenation catalyst, which comprises a metal supported on an oxide phase, followed by a second hydrogenation stage in which the reaction mixture from the first stage is further hydrogenated to a conversion of up to 100% at a temperature of between about 80° C. to 180° C., preferably about 100° C. to 150° C., in the presence of an activated carbon-supported metal hydrogenation catalyst. The temperature in the second hydrogenation stage is greater than the temperature in the first hydrogenation stage. Preferably, the temperature of the second hydrogenation stage is about 10° C. to 100° C., preferably about 20° C. to 60° C., higher than the temperature in the first hydrogenation stage.

The process of the current invention avoids the high-temperature leaching problems of certain oxide support materials, such as $SiO_2$, as well as the deactivation problems of the activated carbon-supported catalysts in the first, low temperature, hydrogenation stage. In addition, the benefit of increased selectivity to 1,3-propanediol is realized by the use of activated carbon-supported catalysts in the second, high-temperature, hydrogenation stage. In a preferred embodiment, the oxide-supported catalyst comprises ruthenium on $SiO_2$ or $TiO_2$ and the activated carbon-supported catalyst comprises ruthenium or palladium on activated carbon.

DETAILED DESCRIPTION OF THE INVENTION

The process of the current invention comprises an improved two-stage process for the hydrogenation of 3-hydroxypropanal. In the first, low temperature, stage, an aqueous HPA solution is hydrogenated in the presence of an oxide-supported metal hydrogenation catalyst at a temperature of between about 30° C. to 80° C., preferably about 40° C. to 80° C. and more preferably about 40° C. to 70° C., until a conversion of greater than about 70% is achieved. Preferably, the conversion in the first stage is at least 90%, more preferably at least 95%. The reaction product from the first hydrogenation stage is heated and further hydrogenated in a second, high temperature, stage at a temperature between about 80° C. to 180° C., preferably about 100° C. to 150° C. and more preferably about 100° C. to 130° C. in the presence of an activated carbon-supported metal hydrogenation catalyst to a conversion of substantially 100%. The temperature in the second hydrogenation stage is greater than the temperature in the first hydrogenation stage. Preferably, the temperature of the second hydrogenation stage is about 10° C. to 100° C. preferably about 20° C. to 60° C., higher than the temperature in the first hydrogenation stage.

It has been found that activated carbon-supported metal hydrogenation catalysts are deactivated more rapidly than oxide-supported metal hydrogenation catalysts under the reaction conditions used in the first hydrogenation stage of the current invention. Surprisingly, in spite of the deactivation observed under the conditions of the low temperature stage, the activated carbon-supported metal catalysts have been found to be preferred for use in the high temperature hydrogenation stage. Activated carbon-supported catalysts have been found to give improved conversion of 2-(2'-hydroxyethyl)-1,3-dioxane to 1,3-propanediol compared to oxide-supported catalysts in the second hydrogenation stage. The rapid deactivation of the activated carbon-supported catalysts found in the low temperature hydrogenation stage is not observed in the high temperature hydrogenation stage. A further advantage of activated carbon-supported catalysts is that the degree of decomposition of 1,3-propanediol in the high temperature stage is reduced compared to oxide-supported catalysts resulting in increased selectivity and yield of 1,3-propanediol.

It has also been found that certain oxide supports, for example $SiO_2$, are not stable in the presence of the acidic reaction solution at the high temperatures used in the second hydrogenation stage. This results in leaching of the support material into the reaction product. The process of the current invention avoids this high temperature leaching problem by using the oxide-supported metal hydrogenation catalysts in the low temperature hydrogenation stage and activated carbon-supported metal catalysts in the high temperature stage. In addition, the oxide-supported catalysts in general have improved activity and service life under the conditions of the low-temperature stage compared to the activated carbon-supported catalysts.

Activated carbon supports suitable for preparation of the carbon-supported metal catalysts are described in R. Schloegl, "Handbook of Heterogenous Catalysis", Vol. 1, page 147, Wiley—VCH 1997. Activated carbons are in general made from carbonized biopolymers which are activated, for example by steam activation or chemical activation, to generate micropores of variable size and shape distribution. The pore volume of the activated carbons depends on the starting material and the activation process used. For example activated carbons-prepared from natural graphite (0.1–20 $m^2/g$), synthetic graphite (0.3–300 $m^2/g$), graphitized carbon blacks (20–150 $m^2/g$), carbon blacks (40–250 $m^2/g$), wood (300–1000 $m^2/g$), peat (400–1200 $m^2/g$), coal (coke) (200–1000 $m^2/g$), coconut shells (700–1500 $m^2/g$) are suitable. Preferably the activated carbons have a surface area of at least about 800 $m^2/g$. Examples of commercially available carbon supports include Norit ROX and Norit CNR 115 activated carbon. Examples of commercially available activated carbon-supported metal catalysts include Degussa catalyst types H 1171 H/W (2 wt % Ru/C; particle size 1.3–2.4 mm) and H 154 H/W (2 wt % Ru/C and 5 wt % Ru/C; particle size 2.3 mm).

When certain oxide-supported metal hydrogenation catalysts are used to hydrogenate solutions containing high concentrations of 1,3-propanediol obtained in the first hydrogenation step of the current invention, it has been found that small quantities of the support material can leach into the reaction mixture, especially when hydrogenation temperatures of greater than about 80° C. are used. This is especially a problem for supports which are less stable to acid solution, such as $SiO_2$, $Al_2O_3$, and MgO. For example, when $SiO_2$-supported catalysts are used in a 3-hydroxypropanal hydrogenation process comprising a first low temperature stage (about 30° C.–80° C.) and a second high temperature stage (about 80° C.–180° C.), leaching silica becomes significant at the higher temperatures. This results in reduced catalyst life and the formation of silica deposits during distillation of the 1,3-propanediol causing fouling of the equipment.

On the other hand, the leaching of the oxide supports is not a significant problem under the conditions of the low temperature hydrogenation stage of the current invention. In addition, certain oxide-supported catalysts, especially those of ruthenium, exhibit improved catalyst life in the first stage when compared to activated carbon-supported catalysts.

Examples of oxide materials which are suitable for use as the oxide phase for the catalyst used in the low temperature stage hydrogenation include $TiO_2$, $SiO_2$, $Al_2O_3$ and/or mixed oxides comprising at least two members selected from the group consisting of $TiO_2$, $SiO_2$, and $Al_2O_3$, for example, aluminum silicate. Other suitable oxide phases include silica gel, MgO, zeolites and/or zirconium dioxide. Such substances are described, for example, in *Catalyst Supports* and *Supported Catalysts* by Alvin, B., Stiles Verlag, Butterworths 1987, Chapters 2 and 3. It is also possible to use mixtures of oxide phases as the support material in the first stage. Preferred oxide phases useful in the first hydrogenation stage are $SiO_2$ and $TiO_2$. Aluminum oxide and magnesium oxide are less preferred.

The titanium dioxide used may be a pyrogenically produced titanium dioxide, particularly titanium dioxide produced by flame hydrolysis. The pyrogenic titanium dioxide used may, for example, be obtained from titanium tetrachloride by flame hydrolysis and having a BET surface area of 40 to 60 $m^2/g$ and a total pore volume of 0.25 to 0.75 ml/g, an average primary particle size of 20 nm, a density of 3.7 g/cm³ and an X-ray structure of 20 to 40% rutile and 80 to 60% anatase and is contaminated with less than 0.5 wt. % of silicon dioxide, aluminum oxide, and iron oxide. Pyrogenic titanium oxide. such as the material P25 from Degussa. is particularly suitable as a support for the catalytically active component, and has an elevated BET specific surface area of on average 50 m²/g (measured according to DIN 66131).

The oxides may be shaped into moldings such as, for example, pellets, granules, or extrudates using methods known in the art, such as those described in U.S. Pat. No. 5,364,984.

Catalytically active metals which are suitable for use in preparing the activated carbon- and oxide-supported catalysts for use in the process of the current invention include ruthenium, platinum, palladium and combinations thereof. More than one metal can be used in preparing the supported catalysts. The metal is disposed on the support in a quantity of from about 0.1 to 20 wt %, preferably about 0.1 to 10 wt %, most preferably about 0.5 to 5 wt % relative to the weight of the oxide or activated carbon support. A catalyst having a lower metal content can be used in the second, high temperature reaction stage, compared to the metal content of the catalyst used in the first, low temperature, stage.

The oxide and activated carbon supports can be coated with metal by means of the Incipient Wetness Method, published in *Preparation of Catalyst*, Delmon, B., Jacobs, P. A., Poncald, G. (eds.), Amsterdam Elsevier, 1976, Page 13. To this end, the water absorption capacity of the support is determined. For example, in preparing ruthenium catalysts, an aqueous ruthenium chloride solution is prepared which has a concentration corresponding to the subsequent ruthenium coating. The support is loaded with the aqueous ruthenium chloride solution in accordance with its water absorption capacity such that the entire quantity of the solution is absorbed. The loaded support is then dried, preferably at about 20° to 100° C. at atmospheric pressure in an inert gas atmosphere, such as neon, helium, argon, nitrogen or in air. The drying step may also be conducted under pressure or vacuum. The dried impregnated support is then reduced with hydrogen to form metallic ruthenium, preferably at a temperature of about 100° to 500° C. for a period of 20 minutes to 24 hours, generally at atmospheric pressure and a hydrogen concentration of 1 to 100% as a mixture with nitrogen. The reduced catalyst is then optionally washed until free of chloride preferably to <100 ppm Cl⁻. This preparation provides a fine subdivision of the metal on the catalyst carrier, with crystallite sizes generally between about 1 and 5 nm as measured by transmission electron microscopy.

The hydrogenation is carried out using the methods disclosed in U.S. Pat. No. 5,334,778, incorporated herein by reference. For example, stirred reactors or flow reactors can be used. A fixed-bed hydrogenation reactor is particularly suitable for conducting the hydrogenation on an industrial scale. In such a reactor, the liquid reaction mixture flows or trickles over the fixed-bed catalyst together with the hydrogen introduced. To ensure good distribution of the hydrogen in the reaction mixture and uniform distribution of the gas/liquid mixture over the entire cross-section of the fixed bed, the liquid reaction mixture and hydrogen can be passed together through static mixers before the catalyst bed. Trickle bed reactors are particularly preferred and are described in Kirk-Othmer Encyclopedia of Chemical Technology, Third Edition, Volume 19, pages 880–914 (especially page 884). The reactor is equipped in such a way that a reaction temperature of between about 30° C. and 80° C., preferably about 40° C. to 80° C., is established and can be maintained in a first stage containing the oxide-supported catalyst and a reaction temperature of about 80° C. to 180° C., preferably about 100° C. to 150° C., is established and can be maintained in a second stage containing the activated carbon-supported catalyst. The catalyst bed in the first stage preferably makes up about 50–95%, more preferably 75–90%, of the total catalyst bed volume with the remaining volume of the catalyst bed comprising the activated carbon-supported catalyst of the second stage. The temperature in each of the two stages can be maintained substantially constant or can have an increasing temperature profile within the specified temperature range for each stage. A single reactor having the appropriate temperature profile or two or more separate reactors in series can be used. There is a heating zone between the first and second stages in order to increase the temperature to the desired value for the second stage reaction.

The 3-hydroxypropanal is generally fed to the reactor as an aqueous solution having a 3-hydroxypropanal concentration of between 2 and 20 wt % preferably between 5 and 15 wt %, based on the weight of water and feed, and a pH between about 2.5 and 7.0, preferably between about 3.5 and 5.5. In continuous processes, liquid hourly space velocities between about 0.1 and 10 h⁻¹ are preferred. The hydrogenation reaction is conducted at a hydrogen pressure of about 5 to 300 bar, preferably at a hydrogen pressure of less than about 90 bar, more preferably from about 10 bars to 60 bars.

EXAMPLES

Examples 1–4 and Comparative Examples A–B

These examples demonstrate the greater deactivation of activated carbon-supported catalysts compared to oxide-supported catalysts under conditions of the low temperature stage of the process of the current invention.

The catalysts were tested under steady-state conditions in order to ascertain long-term performance. Hydrogenation was performed continuously in a trickle bed apparatus (Kirk-Othlmer Encyclopedia of Chemical Technology, Third Edition, Volume 19, pages 880–914 (especially page 884) having a reactor volume of 140 ml. The apparatus consisted of a liquid vessel, the fixed bed reactor, and a liquid separator. The reaction temperature was adjusted by means of a heat transfer medium/oil circuit. The pressure and hydrogen stream were electronically controlled. The aqueous 3-hydroxypropanal solution was apportioned to the hydrogen stream with a pump and the mixture introduced into the top of the reactor (trickle bed operation). Once the mixture had passed through the reactor, the resultant product was removed from the separator at regular intervals. In every case, 50 ml of catalyst was used and the 3-hydroxypropanal concentration in the feed solution was 10 wt. %, with a pH of about 4.0. The hydrogenation temperature was 40° C., the hydrogen pressure 40 bar, and the liquid hourly space velocity, LHSV, was 1.0 h⁻¹. Table 1 summarizes the results of the tests according to various examples. The residual 3-hydroxypropanal concentration in the reaction product was measured by GC and used in calculating the reported conversions. In all examples, the selectivity was greater than 98% (1,3-propanediol concentration measured by gas chromatography).

The catalysts were prepared according to the following method:

1. The water absorption of the support was determined in g of H₂O per 100 g of support.
2. RuCl₃ was dissolved in distilled water for loading 250 ml of support (see Table 1).

3. 250 ml of support were introduced into a coating pan and the $RuCl_3$ solution was poured over the support while the pan was rotating.
4. The coated support was dried for 16 hours in air at room temperature and then heated to 200° C. in air in a tube furnace.
5. The catalyst was then reduced with hydrogen at 200° C. for 8 hours followed by cooling in hydrogen until the catalyst reached room temperature.
6. The reduced catalyst was washed until free of chloride with three 40 ml portions of distilled water.

The supports used had the following characteristics:

Support 1: Silica gel from Grace Davison (Baltimore. Md.) (0.8–1.2 mm)
Name: V432

Support 2: Activated carbon from Norit (Holland) (diameter 2.3 mm)
Name: Norit CNR 115 (olive stones)

Support 3: Activated carbon from Norit (diameter 0.8 mm)
Name: Norit ROX (peat carbon)

Support 4: Titanium dioxide P25 produced pyrogenically by flame hydrolysis from Degussa AG. (Frankfurt, Germany) The support was tempered (950° C. for 12 hrs) and extrusion formed as described in EP 535 565.

Support 5: $Al_2O_3$ from Rhone-Poulenc (France) (diameter 1.1–1.3 mm)
Name: Spheralite 521

The following conditions were maintained during coating of the supports:

TABLE 1

| Support | | Water Absorption (g/100 g of Support) | Support (g) | $RuCl_3$ (g) | Water (g) |
|---|---|---|---|---|---|
| Support 1 | $SiO_2$ V432 | 126 | 115 | 11.8 | 145 |
| Support 2 | Norit 1 Extra | 67 | 105 | 10.8 | 56 |
| Support 3 | Norit ROX 0.8 | 80 | 107 | 11.1 | 68 |
| Support 4 | $TiO_2$ EP 0 535 565 | 25 | 100 | 10.2 | 14 |
| Support 5 | $Al_2O_3$ | 74 | 100 | 22.8 | 52 |

TABLE 2

| No. | Catalyst | Support | Operating Time (h) | Conversion (%) |
|---|---|---|---|---|
| A | 5% Ru/ activated carbon | Support 2 | 26 | 71 |
| | | | 216 | 47 |
| B | 5% Ru/ activated carbon | Support 3 | 24 | 99.7 |
| | | | 96 | 60 |
| 1 | 5% Ru/$TiO_2$ | Support 4 | 19 | 84 |
| | | | 233.5 | 84 |
| 2 | 5% Ru/$SiO_2$ | Support 1 | 48 | 90 |
| | | | 434 | 89 |
| 3 | 10% Ru/$Al_2O_3$ | Support 5 | 72 | 79 |
| | | | 240 | 77 |
| 4 | 2% Pt/$TiO_2$ | Support 4 | 20 | 60 |
| | | | 300 | 45 |

Comparison of the results for Comparative Examples A and B (activated carbon-supported catalysts) to the results for Examples 1–4 (oxide-supported catalysts) shows that the activated carbon-supported catalysts exhibit poorer long-term stability than the oxide-supported catalysts under conditions of the low temperature stage of the process of the current invention. Although the Ru/activated carbon support used in comparative Example B had high initial activity (conversion after 24 h operating time of 99.7%), the conversion decreased by almost 40% over an additional operating time of 72 hours.

Of the oxide catalysts used in these examples, the oxide-supported ruthenium catalysts showed essentially no tendency to be deactivated, with conversion remaining substantially constant over an operating time of greater than 200 hours. The Pt/$TiO_2$ catalyst used in Example 4 had lower initial activity than the Ru/C and Ru/oxide catalysts, however the conversion decreased less rapidly with time compared to the Ru/C catalysts. The conversion was reduced by about 25% after 280 hours of operation for the Pt/$TiO_2$ catalyst versus a 33% and 40% decrease for the activated carbon-supported catalysts of Examples A and B.

Example 5 and Comparative Example C

These examples demonstrate the lower stability of $SiO_2$-supported ruthenium catalysts compared to $TiO_2$-supported ruthenium catalysts under the reaction conditions of the high temperature stage of the process of the current invention.

The reactor and conditions used in these examples was similar to that described above for Examples 1–4 except that the liquid hourly space velocity (LHSV) was 2 $h^{-1}$. The hydrogen pressure was 40 bar. A 5 wt % Ru/$SiO_2$ catalyst was used in Comparative Example C and 5 wt % Ru/$TiO_2$ catalyst was used in Example 5. The 5 wt % Ru/$SiO_2$ catalyst was prepared using the method of Examples 1–4, using X 239 $SiO_2$, commercially available from Grace Davison, having a particle size of 1.0–2.0 mm. The 2 wt % Ru/$TiO_2$ catalyst was prepared using Degussa P25 $TiO_2$ having a particle size of 1.0 mm. The method of Examples 1–4 was used to impregnate the support. The feed solution was prepared by hydrogenating a 10 wt % aqueous 3-hydroxypropanal (HPA) to a conversion of greater than 90% using the above-described 5 wt % Ru/$SiO_2$ catalyst at a temperature of 40° C. and a hydrogen pressure of 40 bar. The metal concentration in the reaction effluent was analyzed by inductively coupled plasma-optical emission spectroscopy and the results are shown in Table 3. Using the $SiO_2$-supported catalyst resulted in severe Si-leaching which leads to decomposition of the catalyst. The $TiO_2$-supported catalyst did not exhibit leaching of Ti under these conditions. It has been found that when $SiO_2$-supported catalysts are used in the high temperature hydrogenation stage that silica deposits form during distillation of the 1,3-propanediol, causing fouling of the equipment. In addition, the $SiO_2$ supported catalyst has a catalyst life of only a few weeks under the conditions of the high temperature stage.

TABLE 3

Metal Concentration in Reaction Effluent

| Example No. | Catalyst | Temp. (° C.) | Operating Time (hours) | Metal Concentration In Effluent (ppm) |
|---|---|---|---|---|
| C | 5 wt % Ru/$SiO_2$ | 130 | 65 | 208 (Si) |
| 5 | 2 wt % Ru/$TiO_2$ | 130 | 45 | <2 (Ti)[a] |

[a]Below detection limit

Examples 6–9 and Comparative Examples D & E

These examples demonstrate higher activity for activated carbon-supported versus $TiO_2$-supported Ru catalysts in the hydrogenation of 2-(2'-hydroxyethyl)-1,3-dioxane (HED) under conditions of the high temperature hydrogenation stage.

The reactor was identical to that described above for Examples 1–4, except that a LHSV of 2 h$^{-1}$ was used. The hydrogen pressure was 40 bar. Operating conditions and results are sunmarized in Table 4 below. The feed solution was an aqueous solution consisting of 18.61 wt % 1,3-propanediol (PDO) and 0.09 wt % HED, except for Comparative Example E in which the feed consisted of an aqueous solution having a PDO content of 19.92 wt % and a HED content of 0.09 wt %. The feed was prepared by hydrogenation of a HPA solution using the 5 wt % Ru/SiO$_2$ catalyst of Comparative Example C at a temperature of 70° C. and a hydrogen pressure of 40 bar. The aqueous 1,3-propanediol solution was concentrated by removing water by distillation. The pH was adjusted by adding a diluted NaOH solution.

TABLE 4

COMPARISON OF ACTIVATED CARBON- AND TiO$_2$- SUPPORTED CATALYSTS FOR HYDROGENATION OF HPA/HED AT 130° C.

| Example No. | Catalyst | Operating Time (h) | Temp (° C.) | Ph Feed | $X_{HED}$ (%) | CPDO.effluent (wt %) |
|---|---|---|---|---|---|---|
| 6 | 2 wt % Ru/carbon$^a$ | 16 | 130 | 4 | 92 | 20.03 |
| 7 | 2 wt % Ru/carbon$^b$ | 43 | 130 | 4 | 100 | 17.61 |
| D | 2 wt % Ru/TiO$_2$$^c$ | 44 | 130 | 4 | 78 | 15.91 |
| 8 | 2 wt % Ru/carbon$^a$ | 28 | 130 | 7 | 42 | 18.58 |
| 9 | 2 wt % Pd/carbon$^d$ | 24 | 130 | 7 | 65 | 18.71 |
| E | 2 wt % Ru/TiO$_2$$^c$ | 68 | 130 | 7 | 19 | 16.60 |

$^a$Degussa catalyst type H 154 H/W, 2% Ru (2.3 mm particle size)
$^b$Degussa catalyst type H 1171 H/W, 2% Ru (1.3–2.4 mm particle size)
$^c$See Example 5
$^d$Carbon support was Carbon Norit RX (1.5 mm particle size). Impregnated with palladium chloride solution using the method of Examples 1–4

The results demonstrate the improved results obtained using activated carbon-supported catalysts in the high temperature stage. At each pH, the Ru/C and Pd/C catalysts showed a higher activity for HED conversion ($X_{HED}$) when compared to the Ru/TiO$_2$ catalyst under conditions of the high temperature hydrogenation stage. In addition, the activated carbon-supported catalysts exhibited a lower tendency to decompose 1,3-propanediol, as evidenced by the higher concentration of PDO in the effluent. The palladium catalysts gave comparable results compared to the ruthenium catalysts, with palladium catalysts showing higher activity in HED hydrogenation and slightly lower activity in PDO decomposition. Although the Ru/TiO$_2$ catalyst did not exhibit leaching of Ti-containing compounds at elevated temperature as demonstrated in Example 5, activated carbon-supported catalysts are preferred in the high temperature stage due to reduced degradation of 1,3-propanediol and improved conversion of HED, increasing the selectivity to 1,3-propanediol. The results also demonstrate that HED conversion is better under acidic conditions.

Examples 10–12

These examples demonstrate the effect of temperature on conversion of 2-(2'-hydroxyethyl)-1,3-dioxane (HED) and on 1,3-propanediol (PDO) decomposition using activated carbon-supported ruthenium and palladium hydrogenation catalysts.

The reactor was identical to that described above for Examples 1–4, except that a LHSV of 2 h$^{-1}$ was used. The hydrogen pressure was 40 bar. Operating conditions and results are summarized in Table 5 below. Results for Examples 7–9, above, are also included in Table 5.

TABLE 5

EFFECT OF TEMPERATURE ON HED CONVERSION AND PDO DECOMPOSITION USING ACTIVATED CARBON-SUPPORTED CATALYSTS IN THE HIGH TEMPERATURE STAGE

| Example No. | Catalyst | Operating Time (h) | Temp (° C.) | pH feed | $X_{HED}$ (%) | $C_{PDO}$, effluent (wt %) |
|---|---|---|---|---|---|---|
| 7 | 2 wt % Ru/carbon$^b$ | 43 | 130 | 4 | 100 | 17.61 |
| 10 | 2 wt % Ru/carbon$^b$ | 113 | 100 | 4 | 90 | 18.66 |
| 8 | 2 wt % Ru/carbon$^a$ | 28 | 130 | 7 | 42 | 18.58 |
| 11 | 2 wt % Ru/carbon$^a$ | 24 | 150 | 7 | 73 | 17.03 |
| 9 | 2 wt % Pd/carbon$^c$ | 24 | 130 | 7 | 65 | 18.71 |
| 12 | 2 wt % Pd/carbon$^c$ | 28 | 150 | 7 | 80 | 18.66 |

$^a$Degussa catalyst type H 154 H/W, 2% Ru (2.3 mm particle size)
$^b$Degussa catalyst type H 1171 H/W, 2% Ru (1.3–2.4 mm particle size)
$^c$Carbon support was Carbon Norit RX (1.5 mm particle size). Impregnated with palladium chloride solution using the method of Examples 1–4

Increasing temperature results in an increase in HED conversion ($X_{HED}$) but also causes an undesirable increase in decomposition of PDO. The palladium catalysts gave superior results at high temperature compared to the ruthenium catalysts. The palladium catalysts show higher activity in HED hydrogenation and lower activity in PDO decomposition, with significantly better results achieved at a temperature of 150° C.

Examples 13–15 and Comparative Example F

These examples demonstrate the improved selectivity to PDO obtained using Ru/C catalysts compared to using Ru/SiO$_2$ in the high temperature stage of a 2-stage process.

The reactor setup used in these examples was similar to that described above for Examples 1–4 except that three independently-heated trickle bed reactors were connected in series. Reactors 1 and 2 each contained 2400 ml of catalyst. Reactor 3 contained 1600 ml. An aqueous 10 wt % 3-hydroxypropanal (HPA) solution was fed to the first reactor at a flow rate which achieved a total LHSV of 1.2 h$^{-1}$. The first and second reactors were heated to 60° C. and 70° C. (80° C. in comparative example F) respectively, to simulate the first (low temperature) adiabatic reaction stage. The first two reactors were filled with the same catalyst (5 wt % Ru/SiO$_2$, see Example C) in comparative example F and with a similar catalyst (5 wt % Ru/SiO$_2$, Grace X 432 SiO$_2$), having the same particle size distribution, in Examples 14–15. The last reactor was heated to 100–130° C. to simulate the second (high temperature) stage. In the Examples of the invention, Ru/C catalysts were used in the third reactor. In Comparative Example F, 5 wt % Ru/SiO$_2$ catalyst was used in all three reactors.

The composition of the HPA feed to Reactor 1 was analyzed by gas chromatography (GC). Operating conditions are summarized in Table 6.

TABLE 6

OPERATING CONDITIONS FOR TWO-STAGE HYDROGENATION

| Example No. | Catalyst in Reactors 1 & 2 | Catalyst in Reactor 3 | Temp. in Reactor 3 (° C.) | Reactor 3 Operating Time (h) |
|---|---|---|---|---|
| 13 | 5 wt % Ru/SiO$_2$ | 2 wt % Ru/C[a] | 100 | 12 |
| 14 | 5 wt % Ru/SiO$_2$ | 2 wt % Ru/C[a] | 100 | 156 |
| 15 | 5 wt % Ru/SiO$_2$ | 2 wt % Ru/C[a] | 120 | 350 |
| F | 5 wt % Ru/SiO$_2$ | 5 wt % Ru/SiO$_2$ | 100 | 321 |

[a]degussa catalyst type H 1171 H/W, 2% Ru (1.3–2.4 mm particle size)

The compositions of the reactor effluents from Reactor 2 and Reactor 3 were also analyzed by gas chromatography (GC) to determine the concentrations of HPA, HED, and PDO. Using the thus obtained HPA concentrations in the feed and Reactor 2 or Reactor 3 effluents, the overall conversion of HPA (XHPA) after Reactor 2 or Reactor 3 was calculated. Using the GC analysis for PDO, HED and HPA concentrations in the effluents of Reactor 2 and Reactor 3, the yield of 1,3-propanediol after Reactor 2 and Reactor 3 was calculated as $Y_{PDO}=X_{HPA} \times S_{PDO}/100$ (S=Selectivity). The "residual carbonyls", which is defined as $\Sigma$ HPA+HED, were calculated for Reactors 2 and 3. These results are reported in Table 7.

TABLE 7

HPA CONVERSION, YIELD OF PDO AND RESIDUAL CARBONYLS FOR TWO-STAGE HYDROGENATION

| Example No. | Reactors included | $X_{HPA}$ (%) | $Y_{PDO}$ (%) | Residual Carbonyls (%) |
|---|---|---|---|---|
| 13 | Reactors 1 & 2 | >99.9 | 92.8 | 5.5 |
|  | Reactors 1, 2 & 3 | >99.9 | 98.9 | <0.01 |
| 14 | Reactors 1, 2 & 3 | >99.9 | >99.7 | 0.13 |
| 15 | Reactors 1 & 2 | 98.8 | 89.2 | 8.9 |
|  | Reactors 1, 2 & 3 | >99.9 | >98.8 | 0.03 |
| F | Reactors 1 & 2 | >99.9 | 88.6 | 5.57 |
|  | Reactors 1, 2 & 3 | >99.9 | 93.5 | 0.73 |

Example 13–14 demonstrate that even after 350 hours of operating time, the Ru/C catalyst continued to have high activity for conversion of 3-hydroxypropanal and 2-(2'-hydroxyethyl)-1,3-dioxane. They also show that no significant deactivation occurs over this time period.

Although the total conversion of HPA and HED was high for all of the examples, only the examples of the current invention resulted in high yield of PDO after Reactor 3 (high temperature stage) combined with essentially complete conversion of carbonyls. A much higher percentage of the HED and HPA in the Reactor 2 effluent were reacted in Reactor 3 to form PDO using Ru/C catalysts compared to Ru/SiO$_2$. In Example F, significant decomposition of the 1,3-propanediol in Reactor 3 occurred, resulting in a low yield of PDO.

What is claimed is:

1. A process for the production of 1,3-propanediol by catalytically hydrogenating an aqueous solution of 3-hydroxypropanal comprising the steps of:

passing the 3-hydroxypropanal solution to a first hydrogenation stage and hydrogenating at a temperature of 30° C. to 80° C. to a 3-hydroxypropanal conversion of at least 70% in the presence of a first hydrogenation catalyst, the first hydrogenation catalyst comprising a first metal supported on an oxide phase; and passing the reaction solution obtained from the first hydrogenation stage to a second hydrogenation stage and hydrogenating at a temperature of about 80° C. to 180° C. to a 3-hydroxypropanal conversion of up to 100% in the presence of a second hydrogenation catalyst comprising a second metal on an activated carbon support, where the hydrogenation temperature of the second stage is greater than the hydrogenation temperature of the first stage.

2. The process of claim 1 wherein the conversion in the first hydrogenation stage is at least 90%.

3. The process of claims 1 or 2 wherein the oxide phase is selected from the group consisting of TiO$_2$, SiO$_2$, Al$_2$O$_3$, MgO, zeolites, ZrO$_2$, and mixed oxides, said mixed oxides comprising at least two members selected from the group consisting of TiO$_2$, SiO$_2$, and Al$_2$O$_3$.

4. The process of claim 1 wherein the oxide phase is selected from the group consisting of SiO$_2$, Al$_2$O$_3$, MgO and mixtures thereof.

5. The process of claim 4 wherein the first metal is selected from the group consisting of ruthenium and platinum and the second metal is selected from the group consisting of ruthenium, palladium, and platinum.

6. The process of claim 5 wherein the second metal is selected from the group consisting of ruthenium and palladium.

7. The process of claim 6 wherein the first hydrogenation catalyst comprises ruthenium on SiO$_2$.

8. The process of claim 7 wherein the second hydrogenation catalyst comprises ruthenium on activated carbon.

9. The process of claim 1, wherein the hydrogenation is carried out in a fixed-bed hydrogenation reactor containing the first hydrogenation catalyst in a first catalyst bed and the second hydrogenation catalyst in a second bed, the first catalyst bed making up 50 to 95 volume percent of the total catalyst bed, the temperature in the first bed being in the range of 30° C. to 80° C., and the temperature in the second bed being in the range of 80° C. to 180° C.

10. The process of claim 1 wherein the first hydrogenation stage and second hydrogenation stages are carried out in separate fixed bed hydrogenation reactors.

* * * * *